United States Patent
Itu et al.

(10) Patent No.: US 10,595,790 B2
(45) Date of Patent: Mar. 24, 2020

(54) METHOD AND SYSTEM FOR PERSONALIZED NON-INVASIVE HEMODYNAMIC ASSESSMENT OF RENAL ARTERY STENOSIS FROM MEDICAL IMAGES

(71) Applicant: Siemens Healthcare GmbH, Erlangen (DE)

(72) Inventors: Lucian Mihai Itu, Brasov (RO); Tiziano Passerini, Plainsboro, NJ (US); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 948 days.

(21) Appl. No.: 14/971,184

(22) Filed: Dec. 16, 2015

(65) Prior Publication Data

US 2016/0166209 A1 Jun. 16, 2016

Related U.S. Application Data

(60) Provisional application No. 62/092,597, filed on Dec. 16, 2014.

(51) Int. Cl.
*A61B 5/05* (2006.01)
*A61B 5/00* (2006.01)
(Continued)

(52) U.S. Cl.
CPC ............ *A61B 5/7278* (2013.01); *A61B 5/026* (2013.01); *A61B 5/02028* (2013.01);
(Continued)

(58) Field of Classification Search
CPC . A61B 2576/02; A61B 5/02028; A61B 5/022; A61B 5/024; A61B 5/026;
(Continued)

(56) References Cited

U.S. PATENT DOCUMENTS

| | | | |
|---|---|---|---|
| 2009/0268954 A1* | 10/2009 | Niinuma | G06T 7/0012 382/128 |
| 2014/0073976 A1† | 3/2014 | Fonte | |
| 2015/0065864 A1* | 3/2015 | Sharma | A61B 5/0263 600/416 |

FOREIGN PATENT DOCUMENTS

WO    WO 2010/148411    * 12/2010

OTHER PUBLICATIONS

Tullus et al., "Imaging in the evaluation of renovascular disease", Pediatr Nephrol, 2010 (Year: 2010).*

(Continued)

*Primary Examiner* — Christopher L Cook

(57) ABSTRACT

A method and system for personalized non-invasive assessment of renal artery stenosis for a patient is disclosed. Medical image data of a patient is received. Patient-specific renal arterial geometry of the patient is extracted from the medical image data. Features are extracted from the patient-specific renal arterial geometry of the patient. A hemodynamic index is computed for one or more locations of interest in the patient-specific renal arterial geometry based on the extracted features using a trained machine-learning based surrogate model. The machine-learning based surrogate model is trained based on features extracted from synthetically generated renal arterial geometries.

39 Claims, 10 Drawing Sheets

(51) Int. Cl.

| | |
|---|---|
| A61B 5/026 | (2006.01) |
| G06T 7/00 | (2017.01) |
| A61B 5/02 | (2006.01) |
| A61B 6/00 | (2006.01) |
| A61B 6/03 | (2006.01) |
| G16H 50/50 | (2018.01) |
| A61B 5/20 | (2006.01) |
| A61B 5/022 | (2006.01) |
| A61B 5/145 | (2006.01) |
| A61B 8/08 | (2006.01) |
| A61B 5/055 | (2006.01) |
| A61B 5/024 | (2006.01) |

(52) U.S. Cl.
CPC ............ *A61B 5/489* (2013.01); *A61B 5/4848* (2013.01); *A61B 6/032* (2013.01); *A61B 6/463* (2013.01); *A61B 6/504* (2013.01); *A61B 6/5217* (2013.01); *G06T 7/0012* (2013.01); *G16H 50/50* (2018.01); *A61B 5/022* (2013.01); *A61B 5/024* (2013.01); *A61B 5/055* (2013.01); *A61B 5/14546* (2013.01); *A61B 5/201* (2013.01); *A61B 5/743* (2013.01); *A61B 6/03* (2013.01); *A61B 6/481* (2013.01); *A61B 6/507* (2013.01); *A61B 8/0891* (2013.01); *A61B 8/483* (2013.01); *A61B 8/5223* (2013.01); *A61B 2576/02* (2013.01); *G06T 2207/20081* (2013.01); *G06T 2207/30084* (2013.01); *G06T 2207/30101* (2013.01)

(58) Field of Classification Search
CPC ..... A61B 5/055; A61B 5/14546; A61B 5/201; A61B 5/4848; A61B 5/489; A61B 5/7278; A61B 5/743; A61B 6/03; A61B 6/032; A61B 6/463; A61B 6/481; A61B 6/504; A61B 6/507; A61B 6/5217; A61B 8/0891; G06T 2207/20081; G06T 2207/30084; G06T 2207/30101; G06T 7/0012

See application file for complete search history.

(56) References Cited

OTHER PUBLICATIONS

Maisel et al., "Biomarkers in kidney and heart disease", Nephrol Dial Transplant, 2011 (Year: 2011).*
Simon, N. et al., Clinical characteristics of renovascular hypertension, The Journal of the American Medical Association , vol. 220,pp. 1209-1218, 1972.
Hansen, K. J. et al., Prevalence of renovascular disease in the elderly : a population based study, Journal of Vascular Surgery, vol. 36, pp. 443-451, 2002.
Olin, J. W. et al., Prevalence of atherosclerotic renal artery stenosis in patients with atherosclerosis elsewhere, The American Journal of Medicine, vol. 88, pp. 46-51 (abstract), 1990.
Missouris, C. G. et al., Renal artery stenosis: a common and important problem in patients with peripheral vascular disease, The American Journal of Medicine, vol. 96, pp. 10-14, 1994.
Valentine , R. J. et al., The coronary risk of unsuspected renal artery stenosis, Journal of Vascular Surgery, vol. 18, pp. 433-440, 1993.
World Health Organization, Global health risks, WHO Library Cataloguing-in-Publication Data: 2009.
Beard , D. A., Tautology vs. Physiology in the Etiology of Hypertension, Physiology, vol. 28, pp. 270-271, 2013.
Safian, R. D. et al., Renal artery stenosis, New England Journal of Medicine, vol. 344, pp. 431-442, 2001.
Mounier-Vehier, C. et al., Changes in renal blood flow reserve after angioplasty of renal artery stenosis in hypertensive patients, Kidney International, vol. 65, pp. 245-250, 2004.
Hirsch, A. I . et al., ACC/AHA 2005 guidelines for the management of patients with peripheral arterial disease: executive summary. A collaborative report from the American Association for Vascular Surgery/Society for Vascular Surgery , Society for Cardiovascular Angiography and Interventions, Society for Vascular Medicine and Biology , Society for Interventional Radiology, and the ACC/AHA taskforce on practice guidelines, Journal of the American College of Cardiology, vol. 47, pp. 1239-1312, 2006.
Jones, N. J. et al., Usefulness of translesional pressure gradient and pharmacological provocation for the assessment of intermediate renal artery disease, Catheterization and Cardiovascular Interventions, vol. 68, pp. 429-434, 2006.
Leesar, M.A. et al., Prediction of hypertension improvement after stenting of renal artery stenosis comparative accuracy of translesional pressure gradients, intravascular ultrasound, and angiography, Journal of the American College of Cardiology, vol. 53, pp. 2363-2371, 2009.
Siddiqui, T. S. et al., Renal hemodynamics: theory and practical tips, Catheterization and Cardiovascular Interventions, vol. 69, pp. 894-901, 2007.
Mangiacapra, F. et al., Translesional pressure gradients to predict blood pressure response after renal artery stenting in patients with renovascular hypertension, Cardiovascular Interventions, vol. 6, pp. 537-542, 2010.
Subramanian, R. et al., Renal fractional flow reserve: a hemodynamic evaluation of moderate renal artery stenoses, Catheterization and Cardiovascular Interventions, vol. 64, pp. 480-486, 2005.
De Bruyne, B. et al. Assessment of renal artery stenosis severity by pressure gradient measurements, Journal of the American College of Cardiology, vol. 48, pp. 1851-1855, 2006.
Mitchell, J. A. et al., Predicting blood pressure improvement in hypertensive patients after renal artery stent placement: renal fractional flow reserve, Catheterization and Cardiovascular Interventions, vol. 69, pp. 685-689, 2007.
Petraco, R. et al., Hybrid iFR-FFR decision-making strategy: implications for enhancing universal adoption of physiology-guided coronary revascularization, EuroIntervention, vol. 8, pp. 1157-1165, 2012.
Bock, A. et al., Pressure dependent modulation of renin release in isolated perfused glomeruli, Kidney International, vol. 41, pp. 275-280, 1992.
Margey, R. et al., Atherosclerotic renal artery stenosis and renal artery stenting: an evolving therapeutic option, Expert Review of Cardiovascular Theraphy, vol. 9, pp. 1347-1360, 2011.
Beregi, J. P. et al., Doppler flow wire evaluation of renal blood flow reserve in hypertensive patients with normal renal arteries, Cardiovascular and Interventional Radiology, vol. 23, pp. 340-346, 2000.
Manoharan, G. et al., Assessment of renal flow and flow reserve in humans, Journal of the American College of Cardiology, vol. 47, pp. 620-625, 2006.
Bittl, J., Damage control for renal artery stenting, Circulation, vol. 117, pp. 2724-2726, 2008.
Atlas, S.A., The renin-angiotensin aldosterone system: pathophysiological role and pharmacologic inhibition, Journal of Managed Care Pharmacy, vol. 13, pp. 9-20, 2007.
Bazemore, T. et al., Relation of pulse and systolic and mean blood pressure to severe renal artery stenosis in patients undergoing concurrent coronary and renal angiography, The American Journal of Cardiology, vol. 111, pp. 1547-1551, 2013.
Cebral, J. R. et al., Association of hemodynamic characteristics and cerebral aneurysm rupture, American Journal of Neuroradiology, vol. 32, pp. 264-270, 2011.
Taylor, C. A. et al., Image-based modeling of blood flow and vessel wall dynamics: applications, methods and future directions, Annals of Biomedical Engineering, vol. 38, pp. 1188-1203, 2010.
Haggerty, C. M. et al., Simulating hemodynamics of the Fontan y-graft based on patient-specific in vivo connections, The Journal of Thoracic and Cardiovascular Surgery, vol. 145, pp. 663-670, 2013.

(56) References Cited

OTHER PUBLICATIONS

Shukla, V. et al., Numerical evaluation of increased blood pressure due to Arterial stenoses and atrophy of end organ, International Journal of Mechanical Engineering and Technology, vol. 4, pp. 10-20, 2013.
Bensalah, M. et al., Hemodynamic modeling of the intrarenal circulation, Annals of Biomedical Engineering, vol. 41, pp. 2630-2644, 2013.
Heflin, L. et al., A computational investigation of the geometric factors affecting the severity of renal arterial stenoses, Journal of Biorheology, vol. 23, pp. 102-110 (abstract), 2009.
Kagadis, G. et al., Computational representation and hemodynamic characterization of in vivo acquired severe stenotic renal artery geometries using turbulence modeling; Medical Engineering & Physics, vol. 30, 2008.
Yim, P. et al., Estimation of the differential pressure at renal artery stenoses, magnetic resonance in medicine, vol. 51, pp. 969-977, 2004.
Zhang, W. et al., Hemodynamic analysis of renal artery stenosis using computational fluid dynamics technology based on unenhanced steady-state free precession magnetic resonance angiography: preliminary results, International Journal of Cardiovascular Imaging, vol. 30, pp. 367-375, 2014.
Kapoor, N., Physiological assessment of renal artery stenosis: comparisons of resting with hyperemic renal pressure measurements, Catheterization and Cardiovascular Interventions, vol. 76, pp. 726-732, 2010.
Nordsletten, D. et al., Structural morphology of renal vasculature, American Journal of Physiology—Heart and Circulatory Physiology, vol. 291, pp. 296-309, 2006.
Todd, J., Hemodynamics of renal artery stenosis, Catheterization and Cardiovascular Interventions, vol. 72, pp. 121-124, 2008.
Leesar, M. A., The importance of appropriate renal artery stenting—considerations for diagnosis and treatment of patients with renal artery stenosis, pp. 67-71, 2012.
Herrmann, S. M. et al., Diagnostic criteria for renovascular disease: where are we now?, Nephrology Dialysis Transplantation, vol. 27, pp. 2657-2663, 2012.

\* cited by examiner
† cited by third party

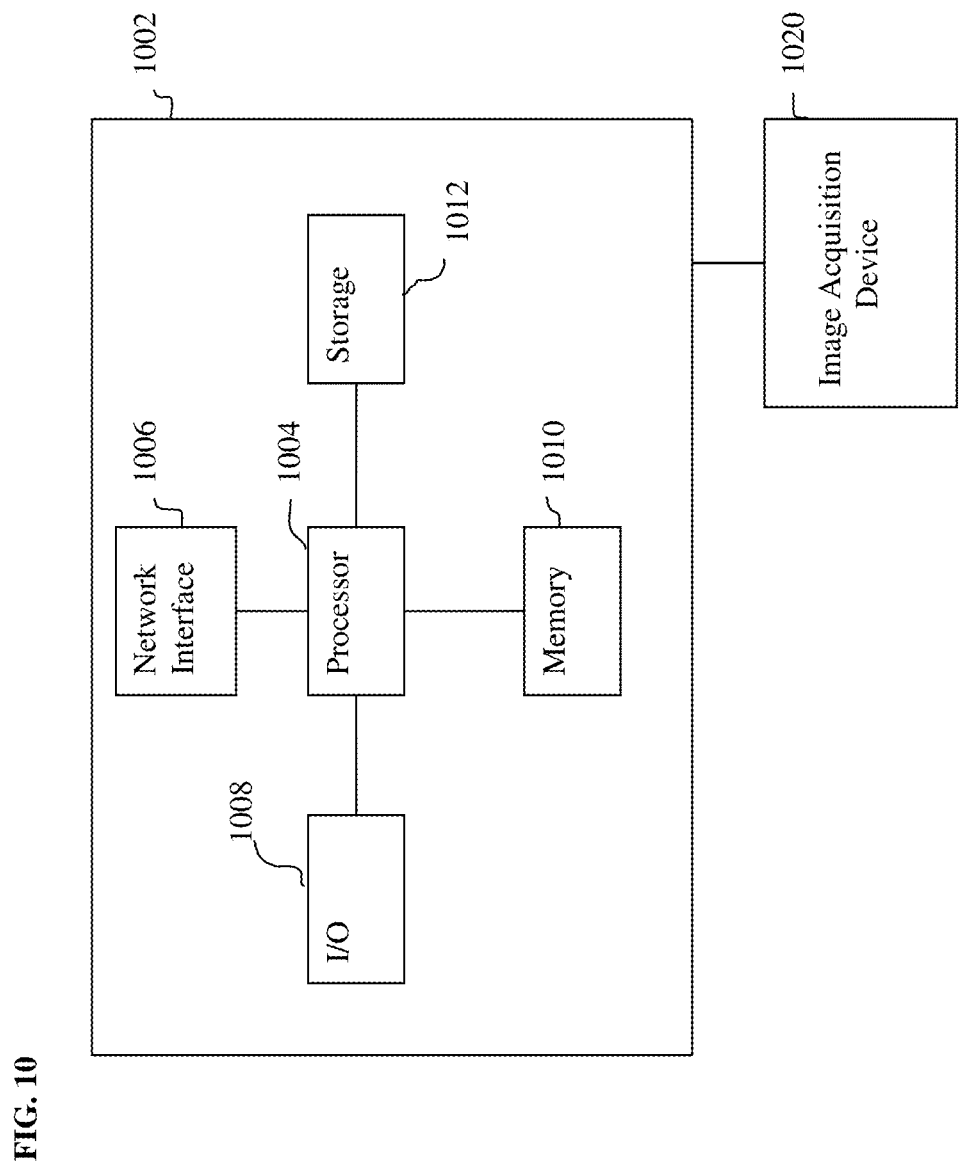

METHOD AND SYSTEM FOR PERSONALIZED NON-INVASIVE HEMODYNAMIC ASSESSMENT OF RENAL ARTERY STENOSIS FROM MEDICAL IMAGES

This application claims the benefit of U.S. Provisional Application No. 62/092,597, filed Dec. 16, 2014, the disclosure of which is incorporated herein by reference in its entirety.

TECHNICAL FIELD

The present invention relates to non-invasive functional assessment of renal artery stenosis, and more particularly, to machine learning based personalized non-invasive hemodynamic assessment of renal artery stenosis from medical image data.

BACKGROUND OF THE INVENTION

Renal Artery Stenosis (RAS) is a cardiovascular pathology consisting of narrowing of the renal artery, and is typically caused by either atherosclerosis or fibromuscular dysplasia. RAS is a major cause of secondary hypertension and is encountered in 0.5 to 5% of all hypotensive patients. In the aging population, RAS has been identified in 6.8% of all individuals over 65 years, with higher prevalence (20-70%) in patients with coronary or peripheral artery atherosclerosis. The World Health Organization considers hypertension to be the most important source of morbidity and mortality among its 19 listed major risk factors affecting global health. However, despite intense research activity over the last 70 years, the etiology of hypertension is still not well understood. If left untreated, RAS progresses relentlessly in time and patient survival rates decrease with increasing RAS severity. RAS can be identified using several medical imaging modalities, such as computed tomography angiography (CTA), magnetic resonance imaging (MRI), abdominal x-ray (AXR), and Doppler ultrasound, and is typically treated either by medical therapy or revascularization (i.e., stenting), with the following goals: blood pressure normalization, improvement of blood pressure control, reduction of antihypertensive medications, preservation of renal function, delay and prevention of the need for kidney transplant, and reduction of cardiovascular events and mortality risks. Revascularization is typically deemed appropriate for hemodynamically significant stenoses defined as: 50-70% diameter stenosis by visual estimation, with a peak trans-stenotic pressure gradient greater than 20 mmHg or a mean gradient greater than 10 mmHG, or greater than 70% diameter stenosis.

In recent years, renal revascularization has evolved from both a procedural and technical point of view. Consequently, there is a growing emphasis of better discerning patients who may benefit from such an intervention. A higher discriminatory power can be reached through the use of function indices, such as trans-stenotic pressure gradients, and renal fractional flow reserve (rFFR), but such functional indices typically require invasive and costly measures, which increase patient risk and strain healthcare budgets. Accordingly, non-invasive techniques for personalized function assessment of renal artery are desirable.

BRIEF SUMMARY OF THE INVENTION

The present disclosure provides methods and systems for personalized non-invasive functional assessment of renal artery stenosis (RAS) from medical images. Embodiments of the present invention provide a non-invasive computational framework which can reliably assess the functional significance of RAS under patient-specific conditions, thus eliminating the need for invasive catheter based pressure measurements. The computational framework utilizes a machine learning based solution in which a data-driven surrogate model is trained based on results obtained from a multiscale physiological model of the renal arterial circulation and the renin-angiotensin-aldosterone system (RAAS). The data-driven surrogate model can predict in real time patient-specific functional hemodynamic indices for RAS from medical image data of a patient.

In one embodiment of the present invention, medical image data of a patient is received. Patient-specific renal arterial geometry of the patient is extracted from the medical image data. Features are extracted from the patient-specific renal arterial geometry of the patient. A hemodynamic index is computed for one or more locations of interest in the patient-specific renal arterial geometry based on the extracted features using a trained machine-learning based surrogate model trained based on features extracted from synthetically generated renal arterial tree geometries.

In another embodiment of the present invention, a plurality of synthetic renal arterial geometries having renal artery stenosis regions with varying geometries are generated. Blood flow simulations are performed for the plurality of synthetic renal arterial geometries. Hemodynamic index values are computed at a plurality of locations in each of the plurality of synthetic renal arterial geometries based on the blood flow simulations. Geometric features are extracted from the plurality of synthetic renal arterial geometries. A surrogate model is trained to map the geometric features extracted from the plurality of synthetic renal arterial geometries to the hemodynamic index values computed at the plurality of locations in each of the plurality of synthetic renal arterial geometries using a machine learning algorithm.

These and other advantages of the invention will be apparent to those of ordinary skill in the art by reference to the following detailed description and the accompanying drawings.

BRIEF DESCRIPTION OF THE DRAWINGS

FIG. 10 is a high-level block diagram of a computer capable of implementing the present invention.

DETAILED DESCRIPTION

The present invention relates to methods and systems for personalized non-invasive functional assessment of renal artery stenosis (RAS) from medical image data. Embodiments of the present invention are described herein to give a visual understanding of the method for non-invasive functional assessment of RAS. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Figure 1:
FIG. 1 illustrates an angiogram showing severe renal artery stenosis in the ostium of the left renal artery.

Renal Artery Stenosis (RAS) refers to the narrowing of the renal artery, and is typically caused by either atherosclerosis or fibromuscular dysplasia. FIG. 1 illustrates an angiogram showing severe renal artery stenosis in the ostium of the left renal artery. In recent years, the assessment of coronary artery disease (CAD) has migrated from an anatomic to a functional assessment, and a similar trend can be observed for RAS, as recent studies have focused on RAS diagnosis exclusively based on functional indices. The pressure gradient guidelines of a peak trans-stenotic pressure gradient greater than 20 mmHG or a mean pressure gradient greater than 10 mmHg are defined for the rest state, but recent studies have evaluated hyperemic indices and thresholds as well. For example, a hyperemic pressure gradient greater than 21 mmHG has been suggested as the strongest predictor of a favorable outcome after stenting. Subsequently, the threshold value of the hyperemic gradient was modified to 20 mmHg, which led to 100% concordance for the prediction of functional severity. Furthermore, similar to the fractional flow reserve (FFR) value in coronary diagnosis, renal fractional flow reserve (rFFR) has been introduced as a functional index for assessing the severity of RAS. rFFR is calculated as the ratio of distal renal pressure to aortic pressure. A cut-off value for rFFR of 0.9 for resting conditions and of 0.8 for hyperemic conditions correlated with improved clinical outcomes. In CAD, although strong clinical data exists showing the superiority of functional decision making for coronary stenosis treatment, the use of FFR is still relatively uncommon. This has been attributed to the requirement of inducing hyperemia and to the additional risks and significant costs in patient care introduced by the use of a guide wire for invasive pressure measurements. A similar trend is expected in the functional diagnosis of RAS.

Renal blood flow regulation is performed by the highly complex renin-angiotensin-aldosterone system (RAAS), which is also an important component of systemic blood pressure regulation. Unlike myocardial ischemia, which appears at increased myocardial oxygen demand (hyperemia), renovascular hypertension and renal dysfunction occur due to chronically abnormal renal perfusion in the resting state. However, functional pressure-based evaluation of RAS has higher discriminatory power at hyperemia. To increase the pressure level at the glomerular cells, RAAS increases the microvascular resistance, leading to a decrease of the flow rate. When hyperemia is induced, the microvascular resistance decreases and flow rate increases. Furthermore, the RAS presence decreases the flow rate due to the additional resistance introduced by the narrowing. No study to date has performed a comprehensive analysis of the individual effects of RAS and renal regulation at rest and hyperemia on pressure, flow, and microvascular resistance.

Blood-flow computations, performed using CFD algorithms, when used in conjunction with patient-specific anatomical models extracted from medical images, can be used for diagnosis, risk stratification, and surgical planning. However, no study to date has validated patient-specific renal blood flow computations at rest or hyperemia, either in healthy or in pathologic subjects. One difficulty of this problem lies in the estimation of personalized inlet and outlet boundary conditions at rest and hyperemia. The personalization framework needs to estimate the inlet flow rate, the microvascular resistance in healthy state, and in the presence of RAS, both at rest and hyperemia. Furthermore, due to the complexity of the renal artery geometry, the computation time of a CFD-based solution may require a considerable amount of processing time, rendering it thus less feasible for a clinical workflow.

Embodiments of the present invention utilize a machine learning based data-driven surrogate model to non-invasively predict personalized functional hemodynamic indices for assessment of RAS. The surrogate model is trained in an offline training stage based on blood flow simulation results obtained using a multiscale physiological model of renal arterial circulation and the RAAS. In order to predict personalized functional hemodynamic indices for RAS of a patient, features are obtained for the patient, including geometric features extracted from medical images of a patient, non-invasive measurements (e.g., cuff-based blood pressure measurements, heart rate measurements, renal biomarkers), and demographic data (age, gender, medical history, etc.), and the trained surrogate model predicts the personalized functional hemodynamic indices based on the features.

Figure 2:
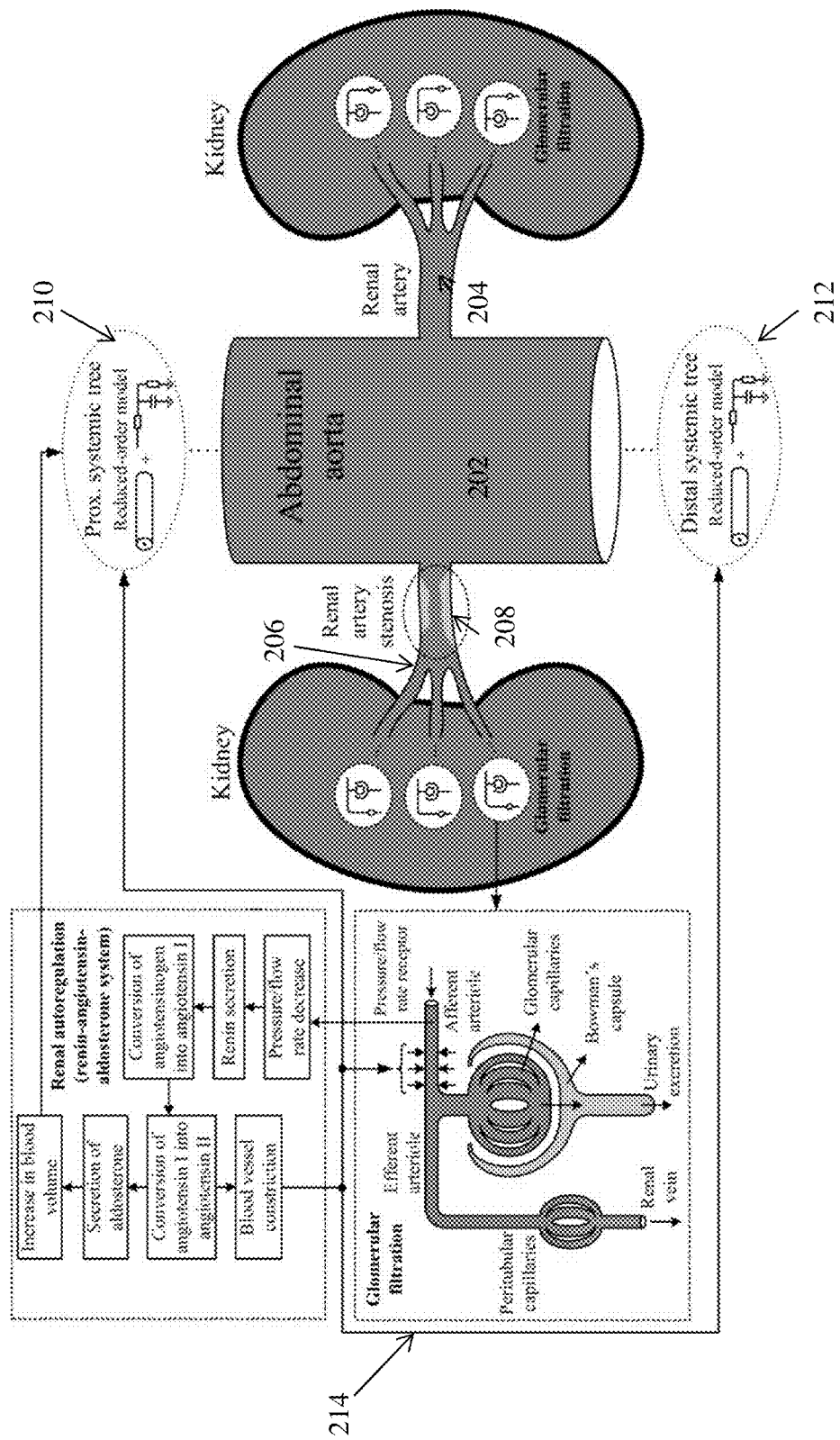
FIG. 2 illustrates a patient-specific multiscale model of renal arterial circulation according to an embodiment of the present invention.

FIG. 2 illustrates a patient-specific multiscale model of renal arterial circulation according to an embodiment of the present invention. In a possible implementation, the patient-specific model of renal arterial circulation can be generated based on renal arterial geometry extracted from medical image data of a patient. Renal blood flow can be simulated in the multi-scale model of renal arterial circulation using computational fluid dynamics (CFD) computations. In the multi-scale model of renal arterial circulation shown in FIG. 2, spatial models are employed for the large arteries, including the abdominal aorta (AA) 202 and the renal arteries 204 and 206. In the multi-scale model of FIG. 2, the geometry of a renal arterial stenosis 208 is modeled in the spatial model of renal artery 206. Reduced order models 210 and 212 are applied for imposing the inlet boundary condition at the proximal AA and the outlet boundary condition at the downstream AA, respectively. According to an advantageous embodiment, the multiscale model includes a renin-angiotensin-aldosterone system (RAAS) and renal microvasculature model 214. The RAAS and renal microvasculature model 214 is a lumped parameter model provides outlet boundary conditions for the renal arteries, at rest and at hyperemia, and affects AA boundary conditions modeled by the reduced-order models 210 and 212. The RAAS and renal microvasculature model 214 simulates renal autoregularization, which is used to maintain blood flow and pressure in the glomerular capillaries to maintain a certain glomerular filtration rate (GFR). The RAAS and renal microvasculature model 214 is used both in the absence and in the presence of RAS, when renal blood flow and pressure are reduced. This is detected by the juxtaglomerular cells, which secrete renin into the circulation. This leads to the generation of angiotensin I (AI), which is converted into angiotensin II (AII). AII causes arteriolar vasoconstriction in the entire body and stimulates the secretion of aldosterone, which increases body fluid volume (leading to an increase of systemic blood pressure). In the kidneys, AII has a greater vasoconstriction effect on the efferent than on the afferent arterioles, and overall it increases arteriolar blood pressure and decreases blood flow rate. Since the constriction effect focuses on the efferent arterioles, glomerular pressure increases and the GFR is maintained. As opposed to coronary microvascular autoregulation, whose goal is to maintain the supply of oxygen to the myocardium at a level given by the oxygen consumption, the renal autoregulation is much more complex: it leads to an increase of microvascular resistance so as to increase the pressure at the glomerular level, which in turn is unknown and cannot be directly measured. The hyperemic flow response can be estimated well for healthy subjects, leading to a 1.5 to 2 fold flow rate increase. In case of RAS multiple aspects are compounded and the final effect of hyperemia is different. In addition to using the patient-specific geometry to personalize the patient-specific multi-scale model of renal arterial circulation, other non-invasive measurements such as renal biomarkers of the patient may be used as well. Examples of renal biomarkers that can be used include: functional markers including serum creatinine, serum crystatin C, and urine albumin; up-regulated proteins including neutrophil gelatinase-associated lipocalin (NGAL), kidney injury molecule 1 (KIM-1), liver-type fatty acid-binding protein (L-FABP), interleukin 18 (IL-18), β-trace protein (BTP), and asymmetric dimethylarginine (ADMA); low-molecular weight proteins such as urine crystatin C; and enzymes including N-acetyl-glucosaminidase (NAG), glutathione-s-transferase (GST), gamma-glutamyl transpeptidase (GGT), alanine aminopeptidase (AAP), and lactate dehydrogenase (LDH). In a possible implementation, the microvascular resistance used to implement the RAAS and renal microvasculature model 214 can be derived as a function of any one or combination of the above described biomarkers. For example, the microvascular resistance can be derived as $R_{micro}=f(NGAL, KIM-1,$ etc.), where f may represent any mathematical operator.

Figure 3:
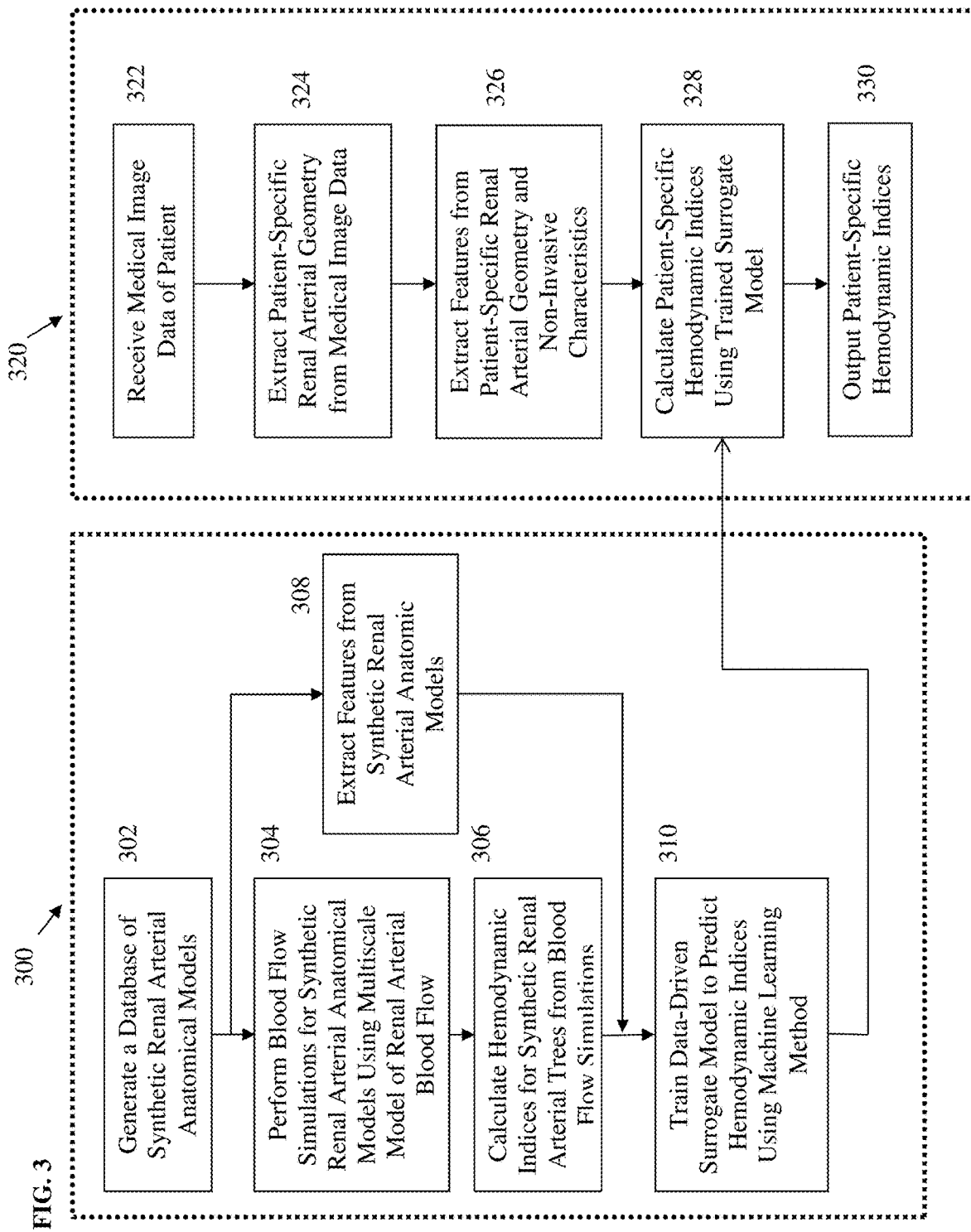
FIG. 3 illustrates a method for personalized non-invasive hemodynamic assessment of renal artery stenosis from medical image data according to an embodiment of the present invention.

FIG. 3 illustrates a method for personalized non-invasive hemodynamic assessment of renal artery stenosis from medical image data according to an embodiment of the present invention. The method of FIG. 3 is a machine learning based method that can be applied to compute hemodynamic indices, such as rFFR and trans-stenotic pressure gradients, at hyperemia and at rest in order to provide a non-invasive functional assessment of RAS severity.

The method of FIG. 3 includes a training phase 300 and a prediction phase 320. The training phase 300 is an offline process, in which one or more data driven surrogate models for predicting hemodynamic indices are trained using a machine learning method. The prediction phase 320 is an online process, whereby one or more patient-specific hemodynamic indices are computed based on patient-specific features extracted from input medical image data of a patient and non-invasive measurements using the trained data driven surrogate model from the training phase 300. Once the training phase 300 is completed, the trained surrogate model is stored, for example in memory or storage of a computer system, and the prediction phase 320 can be repeatedly performed for various patients using the trained surrogate model.

The training phase 300 includes steps 302-310. At step 302, a database of synthetic renal arterial anatomical models is generated. The synthetic renal arterial anatomical models can be generated based on input patient data and/or literature data. For example, the synthetic renal arterial anatomical models may be generated to represent vessel sizes (length, radius, tapering) and bifurcation/trifurcation angles described in literature and/or to represent specific examples of patient data. A large number of synthetic renal arterial anatomical models can be generated by varying the shape, severity, location, and number of stenoses, together with the vessel sizes of the renal arteries. In an exemplary embodiment, the synthetically generated renal arterial trees can be implemented using straight tubes to represent the renal arteries with narrowings in the tubes to represent stensoses or other anomalies in the renal arteries. Other more complex models of the renal artery and stenosis geometry may be used as well. According to an advantageous implementation, the synthetic renal arterial anatomical models are generated in silico, i.e., on a computer, using computer models to generate the synthetic renal arterial trees.

In addition the synthetic renal arterial anatomical models, other non-invasive characteristics associated with each synthetic renal arterial anatomical model, such as pressure estimations, demographic data, and renal biomarkers, are stored in the database. For example, the demographic data can include sex, age, and medical history data. Examples of renal biomarkers that can be used include: functional markers including serum creatinine, serum crystatin C, and urine albumin; up-regulated proteins including neutrophil gelatinase-associated lipocalin (NGAL), kidney injury molecule 1 (KIM-1), liver-type fatty acid-binding protein (L-FABP), interleukin 18 (IL-18), β-trace protein (BTP), and asymmetric dimethylarginine (ADMA); low-molecular weight proteins such as urine crystatin C; and enzymes including N-acetyl-glucosaminidase (NAG), glutathione-s-transferase (GST), gamma-glutamyl transpeptidase (GGT), alanine aminopeptidase (AAP), and lactate dehydrogenase (LDH).

The use of the synthetic data in the training database has several advantages. A very large number of cases can be automatically generated, leading to an extensive databased of training samples covering a large variety of renal arterial stenoses. Complex pathological configurations, such as serial stenoses, multi-branch stenoses, bifurcation stenoses, and diffuse disease, can be generated, and rare pathological cases can be sampled better. The database can be easily extended to different demographic groups, and the training can be iteratively approved with either more data or with better representations of the features.

At step 304, renal blood flow simulations are performed for the synthetic renal arterial anatomical models. In an advantageous embodiment, the blood flow simulations for each of the synthetic renal arterial anatomic models are performed using the patient-specific multi-scale model of renal arterial circulation as described above and illustrated in FIG. 2. A patient-specific multi-scale model of renal arterial circulation is generated for each synthetic renal arterial anatomical model and computational fluid dynamic (CFD) computations are used to simulate renal blood flow and pressure in the multi-scale model of renal arterial blood flow.

In this case, a corresponding multi-scale model of renal arterial circulation is personalized for each of the synthetic renal arterial anatomical models and is thus considered to be "patient-specific" even though the corresponding synthetic renal arterial anatomical model may not represent actual input patient data. Separate CFD simulations for rest state and hyperemia state can be performed for each synthetic arterial anatomical model. The blood flow simulations result in blood flow and pressure values at various locations in the renal arterial circulation model for each of a plurality of time steps.

At step 306, hemodynamic indices are calculated for the synthetic renal arterial anatomical models from the blood flow simulations. In an advantageous embodiment, renal fractional flow reserve (rFFR) can be calculated for multiple sampling points along the renal artery centerline in each of the synthetic renal arterial anatomical models. rFFR can be calculated as the ratio of average distal renal pressure to the average aortic pressure over a cardiac cycle. rFFR can be calculated at rest and at hyperemia. In addition to or instead of rFFR, other hemodynamic indices, such as a pressure gradient over a RAS, can be calculated. For example, a peak pressure gradient over the RAS and the average pressure gradient over the RAS over a cardiac cycle can be calculated both at hyperemia and at rest.

At step 308, features are extracted from the synthetic renal arterial anatomical models. As shown in FIG. 3, step 308 may be performed in parallel with steps 304 and 306, but the present invention is not limited thereto. Various geometric features can be extracted from the synthetic renal arterial anatomical models. In a possible implementation, a centerline tree is constructed for each given synthetic renal arterial anatomical model. The points in the centerline tree are then classified as a start point, ramification points, end points, and interior points. The start point is the first point of the centerline tree corresponding to a renal ostium. A ramification point is a point where the centerline bifurcates into two or more centerline segments. An end point is a point for which no further downstream centerline point exists. An interior point is a point lying between the start point and a ramification points, two ramification points, or a ramification point and the end point. Each segment of the renal arterial tree is classified as a root segment, branch segment, or leaf segment. A root segment is a segment delimited by a start point and a ramification point. A branch segment is a segment delimited by two ramification points. A leaf segment is a segment delimited by a ramification point and an end point. Each renal artery segment (root/branch/leaf) is then divided into one or more segments characterized as anomalous (non-healthy) or non-anomalous (healthy) segments. An anomalous (non-healthy) segment is a segment which has an abnormal luminal narrowing or dilation (e.g., a renal artery stenosis). A non-anomalous (healthy) segment is a segment which has no abnormal luminal narrowing or dilation.

Various features that characterize the geometry of the renal arterial tree can be extracted at various sampling points of each synthetic renal arterial anatomical model. For example, for each RAS (anomalous segment) in the renal arterial tree the following geometric features may be extracted: proximal radius of the stenosis, distal radius of the stenosis, minimum radius of the stenosis, percentage diameter of the stenosis computed from the proximal radius and minimum radius, percentage diameter of the stenosis computed from the distal radius and the minimum radius, total stenosis length, entrance length of the stenosis (length from start of stenosis to location with minimum radius), exit length of the stenosis (length from location with minimum radius to end of stenosis), and minimum radius length (length of the stenosis in the region of minimum radius—a tolerance can be used for detecting the region around the location with minimum radius). Furthermore, various combinations obtained through algebraic, integration, or derivation operations applied to proximal, distal, and minimum radii of the stenosis can also be used as features.

In an advantageous embodiment, the features also include a renal insufficiency weight w and a renal insufficiency score s. The renal insufficiency weight w is a renal insufficiency weight value associated with each renal artery segment (i.e., root, interior, or leaf segment). The renal insufficiency score s is computed for specific non-zero finite length segments of renal artery geometry comprising one or more branches. The renal insufficiency score is computed from a series of geometric properties and from renal insufficiency weights of the particular segments.

Regarding the renal insufficiency weight, w, it can be assumed that the renal insufficiency weight value of each renal segment corresponds to the renal insufficiency weight values of all downstream segments. A three stage local-to-global-to local approach can be used to compute the renal insufficiency weights. In a first local stage, a separate renal insufficiency weight is computed for each renal artery segment. As these renal insufficiency weight values are computed independently, there is no guarantee that the original assumption holds (e.g., the sum of the renal insufficiency weights of two daughter segments is not necessarily equal to the renal insufficiency weight of the parent segment). Accordingly, in a global stage, a global renal insufficiency weight of the entire renal arterial tree is computed by averaging the weight of different segments in different generations. In a final local stage, the global renal insufficiency weight is distributed to the individual segments in a way that satisfies the original assumption.

In the first local stage, a local renal insufficiency weight is independently calculated for each renal artery segment. In particular, for each root segment, branch segment, and leaf segment, the local renal insufficiency weight value can be calculated using:

$$w = k_1 r_{ref}^n, \quad (1)$$

where $r_{ref}$ is the reference radius of the segment, $k_1$ is a proportionality constant, and n is a power coefficient. In exemplary implementations, the power coefficient n may take values between 2 (for large arteries) and 3 (for small arteries). Since, regularly, the radius along the centerline of a segment, r(x), is continuously varying, a mathematical operator $f_1$ is applied to calculate the reference radius value $r_{ref}$ for each renal artery segment:

$$r_{ref} = f_1(r(x)). \quad (2)$$

where r(x) is the radius of the renal artery segment and x is a position along the centerline of the renal artery segment. In a possible implementation, the operator $f_1$ can calculate an average value of healthy radiuses along the entire length of the segment or a part of the segment. When used herein, "healthy radiuses" refer to radiuses of healthy (non-anomalous) portions of a segment. In another possible implementation, the operator $f_1$ can calculate an average value of the healthy radiuses along the entire length of the segment or a part of the segment, excluding the largest x % and the smallest y % of the healthy radius values. In another possible implementation, the operator $f_1$ can calculate the maximum or minimum value of healthy radiuses along the entire length of the segment or a part of the segment. It is to be understood that the operator $f_1$ is not necessarily limited to these operations and other possible calculations can also be used to estimate the reference radius of a segment.

In the global stage, a global renal insufficiency weight value for the entire renal arterial tree (left or right renal arterial tree) is computed based on the local renal insufficiency weights calculated in the first local stage. A respective global renal insufficiency weight for the renal arterial tree is calculated from each generation of segments based on the local renal insufficiency weights of the segments calculated in the first local stage. The root segment of the renal artery tree has a generation number 0, and at each bifurcation the generation number increases by one. A separate estimate for the global renal insufficiency weight of the renal artery tree can be estimated from segments of each generation number. The global renal insufficiency weight estimate for the renal arterial tree calculated using the branches with the generation number g is calculated as follows. Before estimating the global renal insufficiency weight from generation number g, a confidence value $c_i$ is assigned to each segment representing a confidence in the correctness of the estimated reference radius for that segment. The segments can be weighted based on the length of the segment and/or the percentage of the branch that is diseased (anomalous). Accordingly, short segments or entirely diseased segments are assigned low confidence values, while long segments without radius irregularities are assigned large confidence values. The confidence values may be normalized to range between 0 (minimum confidence) and 1 (maximum confidence). A global renal insufficiency weight for the entire renal arterial tree is then estimated based on the segments from generation g using the local renal insufficiency weights $w_i$ calculated for the segments from generation g and the confidence values $c_i$ assigned to those segments using a mathematical operator $f_2$:

$$(w_{global})=f_2(c_i,w_i), \quad (3)$$

where index i refers to all segments from generation g and all leaf segments with a generation number smaller than g. For example, $(w_{global})_g$ for each generation g can be calculated as:

$$(w_{global})_g=\Sigma_i c_i w_i. \quad (4)$$

A plurality of global renal insufficiency weight estimates are calculated by calculating respective a global renal insufficiency weight estimate based on segments from each generation g between $g_{min}$ and $g_{max}$. In an advantageous implementation, the minimum generation level $g_{min}$ can be 0. The maximum generation level can be set to determine how many generations are used in calculating the total rest flow rate of the renal arterial tree. In advantageous implementations, the value for the maximum generation level $g_{max}$ may be set to 3 or 4. Branches of higher generations become increasingly smaller, which makes an accurate estimation of the reference radius and corresponding local ischemic weights using the higher generation branches more difficult. Furthermore, when the renal arterial tree geometry is reconstructed from medical image data (in the prediction phase 320), small side branches may not be accounted for in the model. Hence, the higher the generation number, the higher the number of side branches not been considered will be, leading to a larger error in the flow rate estimation.

A final global renal insufficiency weight of the entire renal arterial tree is calculated from the global renal insufficiency weight estimates calculated from the various generations of segments. To improve accuracy of the final global renal insufficiency weight of the renal arterial tree, the global renal insufficiency weight estimates calculated from multiple different segment generations are used to calculate the final total global renal insufficiency weight value. In particular, the global renal insufficiency weight estimates calculated from each generation g between $g_{min}$ and $g_{max}$ are used to calculate the final global renal insufficiency weight value for the renal arterial tree. Before estimating the final global renal insufficiency weight of the entire renal arterial tree, a confidence value $d_j$ is assigned to each generation number, representing a confidence in the correctness of the global ischemic weight estimate calculated from the segments with the corresponding generation number. Low generation numbers can be assigned large weights, while large generation numbers can be assigned low weights as smaller side branches may be missed in patient-specific renal arterial tree geometry (in the prediction phase 320) as the generation number increases. For example, the confidence values $d_j$ can have an inverse relationship to the generation number. The confidence values $d_j$ may be normalized to range between 0 (minimum confidence) and 1 (maximum confidence). The final global renal insufficiency weight value is estimated as a function of the global renal insufficiency weight estimates for the various generations $(w_{global})_j$ and the corresponding confidence values $d_j$ assigned to the generations using a mathematical operator $f_3$:

$$w_{global}=f_3(d_j,(w_{global})_j), \quad (5)$$

where the index j refers to a generation between $g_{min}$ and $g_{max}$. For example, the global renal insufficiency weight for the renal arterial tree can be calculated as a weighted mean:

$$w_{global} = \frac{\Sigma_j d_j \cdot (w_{global})_j}{\Sigma_j d_j}. \quad (6)$$

In the final local stage, final local renal insufficiency weight values for the segments of the renal arterial tree are computed by distributing the global renal insufficiency weight calculated in the global stage to the individual renal artery segments. The final local renal insufficiency weight is first calculated for each of the leaf segments of the renal arterial tree based on the global renal insufficiency weight of the renal arterial tree. The local renal insufficiency weights for the leaf segments of the renal arterial tree can be calculated by distributing the global renal insufficiency weight of the renal arterial tree over all of the leaf segments based on the reference ratios or the initial renal insufficiency weight values individually calculated for leaf segments. In particular, the local renal insufficiency weight for the each of the renal leaf segments can be calculated as:

$$w_k = \frac{(r_{ref})_k^n}{\Sigma_k (r_{ref})_k^n} w_{global}, \quad (7)$$

where k refers to the leaf segments of the renal arterial tree.

The final local renal insufficiency weight values of the remaining segments of the renal arterial tree are then calculated based on the final local renal insufficiency weights of the leaf segments. The final renal insufficiency weight values of the branch segments and the root segment are calculated as a sum of the downstream leaf segments. That is, for each remaining renal artery segment (root segment and branch segments), the final local renal insufficiency weight is calculated as:

$$w_l=\Sigma_{k_l} w_{k_l}, \quad (8)$$

where l refers to a current renal artery segment and $k_l$ refers to all leaf segments lying downstream from the current segment l.

The renal insufficiency score can be computed for any non-zero finite length renal artery segment or segments which may or may not contain ramifications. The renal insufficiency score is computed differently for non-anomalous (healthy) and anomalous (non-healthy) segments. Non-anomalous segments will have low renal insufficiency scores. For a non-anomalous length of renal artery, the renal insufficiency score can be calculated using the formula:

$$s = k_2 \int_0^L \frac{w(x)}{r(x)^n} dx, \tag{9}$$

where L is the total length of the segment(s), $k_2$ is a proportionality constant, n is a power coefficient, r(x) is the radius which varies along the centerline, and w(x) is the renal insufficiency weight, which can vary along the centerline if ramifications are present.

Anomalous (non-healthy) segments (e.g., stenosis segments) have higher renal insufficiency scores, whereas the higher the severity of the lesion (e.g., stenosis), the higher the renal insufficiency score will be. For a stenosis that stretches along a single root, branch, or leaf segment, the renal insufficiency score is calculated using the formula:

$$s = f_4(r(x))w_l + f_5(r(x))w_l^2, \tag{10}$$

where $f_4$ and $f_5$ are mathematical operators applied to the longitudinally varying radius of the stenosis segment and $w_l$ is the renal insufficiency weight of the segment. Various mathematical operators can be used for $f_4$ and $f_5$. In an exemplary implementation, $f_4$ uses mean of the radius along the stenosis, such that $f_4(r(x)) = k_3 \cdot \overline{r(x)}$, where $\overline{r(x)}$ is the mean of the radius over the stenosis segment and $k_3$ is a proportionality constant. In another exemplary implementation, $f_4$ uses integral of the inverse of the radius, such that $$f_4(r(x)) = k_4 \cdot \int_0^L \frac{1}{r(x)^n} dx,$$

wherein $k_4$ is a proportionality constant, L is the length of the stenosis segment, and n is a power coefficient. $f_5$ may be calculated using the radius at the top and bottom of the stenosis. In one exemplary implementation, $f_5$ is calculated as $$f_5(r(x)) = k_5 \cdot \left( \frac{1}{r_{bottom}^2} - \frac{1}{r_{top}^2} \right),$$

where $k_5$ is a proportionality constant, $r_{top}$ refers to the healthy radius at the proximal end of the stenosis segment, and $r_{bottom}$ refers to the healthy radius at the distal end of the stenosis segment. In another exemplary implementation, $f_5$ is calculated as $$f_5(r(x)) = k_6 \cdot \left( \frac{1}{r_{min}} - \frac{1}{r_{bottom}} \right)^2,$$

where $k_5$ is a proportionality constant, $r_{min}$ refers to the minimum radius of the stenosis segment, and $r_{bottom}$ refers to the healthy radius at the distal end of the stenosis segment. In addition to the renal insufficiency score computed using equation (10), the two components of equation (10) may also be separately used as training features for training the surrogate model, and each component may also be divided into subcomponents which can then be used as features as well. In the case of bifurcation stenoses, i.e., stenoses which stretch over a bifurcation along multiple root, branch, or leaf segments, a separate renal insufficiency score is computed using equation (10) for each root, branch, or leaf segment of the stenosis pertaining to either the parent or the daughter segments.

Based on the renal insufficiency scores of individual segments, multiple features representing cumulative renal insufficiency scores can be computed at any location in the renal arterial tree. Cumulative renal insufficiency scores of multiple segments can be calculated by adding the renal insufficiency scores of the segments together. For a current location in a renal arterial tree (e.g., a sampling point in a synthetically generated renal arterial anatomical model), multiple renal insufficiency score features can be calculated including one or more of the following features:

- Cumulative renal insufficiency score computed from all segments lying between the root segment and the current location;
- Cumulative renal insufficiency score computed from the non-anomalous (healthy) segments lying between the root segment and the current location;
- Cumulative renal insufficiency score computed from the anomalous (non-healthy/pathological/stenosis) segments lying between the root segment and the current location;
- Cumulative renal insufficiency score computed from all segments lying between the current location and a leaf segment. The path from the current location to the leaf segment can for example be determined by choosing at each ramification the path along the main daughter segment, as determined from a combination of properties, such as reference radius, total length downstream, total number of generations downstream, etc.;
- Cumulative renal insufficiency score computed from the non-anomalous (healthy) segments lying between the current location and a leaf segment; and/or
- Cumulative renal insufficiency score computed from the anomalous (non-healthy/pathological/stenosis) segments lying between the current location and a leaf segment.

In addition to the feature extracted from the geometry of the synthetic renal arterial anatomical models, other features including non-invasive measurements, such as pressure measurements, heart rate measurements, and renal biomarkers, and demographic data associated with each synthetic renal arterial anatomical model are also used as features for training the data driven surrogate model for predicting hemodynamic indices.

Returning to FIG. 3, at step 310, a data-driven surrogate model is trained based on the extracted features to predict the hemodynamic indices using a machine learning method. Once the hemodynamic indices for various sampling points in the synthetic renal arterial anatomical models are determined from the blood flow simulations and the features are extracted from the synthetic renal arterial anatomical models and other the non-invasive characteristics (e.g., pressure and heart rate estimations, renal biomarkers, demographic data), a surrogate model that provides mapping between the input features and the hemodynamic indices is determined by using a machine learning algorithm. The type of machine learning algorithm used to train the surrogate model may be a supervised, semi-supervised, transductive, or reinforcement based learning algorithm. For example, machine learning algorithms, such as regression algorithms (linear, non-linear, or logistic), decision trees or graphs, association rule learning, artificial neural networks, support vector machines, inductive logic programming, Bayesian networks, instance-based learning, manifold learning, sub-space learning, deep learning, dictionary learning, etc., may be used to train the machine-learning based surrogate model. According to an advantageous embodiment, the trained surrogate model is a learned data-driven surrogate model that combines the extracted features with various learned weights. A separate surrogate model may be trained for each hemodynamic index or measurement of interest. For example, separate surrogate models can be trained to compute rFFR at rest and hyperemia, average trans-stenotic pressure gradient at rest and hyperemia, and peak trans-stenotic pressure gradient at rest and hyperemia.

In the prediction phase 320 (steps 322-330) of FIG. 3, the trained surrogate model (or models) is used to predict a patient-specific hemodynamic index (such as rFFR) based on patient-specific features extracted from medical image data and non-invasive characteristics of a patient. In the prediction phase 320, at step 322, medical image data of a patient is received. Medical image data from one or multiple imaging modalities can be received. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D, or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient. In an advantageous embodiment, 3D CT angiography (CTA) images are acquired on a CT scanner. The CTA images ensure that the renal vasculature, including the vessel(s) that contain the renal artery stenosis, is adequately imaged using a contrast agent that is injected into the patient.

In addition to the medical image data, non-invasive measurements of the patient can be acquired or input as well. For example, cuff-based blood pressure measurements and heart rate measurements of the patient can be received. Renal biomarker measurements can be received. For example, blood and/or urine of the patient can be tested for one or more renal biomarkers. Examples of such renal biomarkers that can be used include: functional markers including serum creatinine, serum crystatin C, and urine albumin; up-regulated proteins including neutrophil gelatinase-associated lipocalin (NGAL), kidney injury molecule 1 (KIM-1), liver-type fatty acid-binding protein (L-FABP), interleukin 18 (IL-18), β-trace protein (BTP), and asymmetric dimethyl-arginine (ADMA); low-molecular weight proteins such as urine crystatin C; and enzymes including N-acetyl-glucosaminidase (NAG), glutathione-s-transferase (GST), gamma-glutamyl transpeptidase (GGT), alanine aminopeptidase (AAP), and lactate dehydrogenase (LDH).

At step 304, patient-specific renal arterial geometry is extracted from the medical image data of the patient. The patient-specific renal arterial geometry can be patient-specific geometric measurements for a full renal artery tree of the patient or patient-specific geometric measurements for any portion less than the full renal artery tree of the patient. In a possible implementation, the patient-specific renal arterial tree geometry can be patient-specific anatomical measurements of only a left renal artery or a right renal artery. In an advantageous embodiment, the patient-specific renal arterial geometry is extracted by segmenting a patient-specific renal arterial anatomical model from the medical image data, but the present invention is not limited thereto. The patient-specific renal arterial anatomical model may be a patient-specific anatomical model of any portion of the full renal artery tree of the patient. In order to generate the patient-specific renal arterial anatomical model, the renal arteries can be segmented in the 3D medical image data using an automated centerline extraction algorithm. For example, the method for segmenting coronary arteries a CT volume described in United States Published Patent Application No. 2010/0067760, which is incorporated herein by reference, can be adapted to automatically detect renal artery centerlines. Once a renal artery centerline tree is extracted, cross-section contours can be generated at each point of the centerline tree. The cross-section contour at each centerline point gives a corresponding cross-section area measurement at that point in the renal artery. A geometric surface model can then be generated for the segmented renal arteries. For example, methods for anatomical modeling of the coronary arteries described in U.S. Pat. Nos. 7,860,290 and 7,953,266, both of which are incorporated herein by reference, can be similarly used to model renal arteries. In a possible implementation, the renal arterial anatomical model for the patient can be output and displayed, for example on a display screen of the computer system.

In an alternative embodiment, the patient-specific renal arterial geometry can be extracted by extracting geometric measurements of the renal arterial tree directly from the image data without segmenting a full patient-specific renal arterial anatomical model. For example, a renal artery centerline can be detected in the image data as described above, and then a radius of the renal artery can be automatically detected at each centerline point. These geometric measurements can then be used to calculate the geometric features in step 326.

Anomalous (e.g., renal artery stenosis) regions of the renal arteries are identified. For example, renal artery stenosis regions can be automatically segmented in the medical image data or in the patient-specific renal arterial anatomical model. In one embodiment, a machine-learning based method can be used to automatically detect stenosis regions in the medical image data. For example, the method for automatic detection of coronary artery stenosis described in United States Published Patent Application No. 2011/0224542, which is incorporated herein by reference, can be applied for automated renal artery stenosis detection. In another embodiment, renal artery stenosis regions may be automatically detected from the extracted renal artery centerline and radius values of the centerline points by detecting centerline points in which the radius decreases and then increases again beyond a tolerance value. In another embodiment, user input identifying the renal artery stenosis regions can be received, for example, by a user clicking on renal artery stenosis regions of the medical image data or segmented renal artery tree on a display device of a computer system using a user input device.

At step 326, features are extracted from the patient-specific renal arterial geometry and from the patient-specific non-invasive characteristics. In particular, the geometric features described above in connection with step 308 of the training phase 300 are extracted for the patient-specific renal arterial geometry. Such features include the renal insufficiency weights of the various segments of the patient-specific renal arterial tree, the renal insufficiency scores (including multiple cumulative renal insufficiency scores), and geometric measurements of the anomalous/stenosis regions in the patient-specific renal arterial geometry. The calculation of such features from the geometry of the patient-specific renal arterial tree is performed as described above in connection with step 308. In addition, non-invasive measurements of the patient, including cuff-based blood pressure measurements, heart rate measurements, and one or more renal biomarkers, and demographic data of the patient, such as age, sex, and medical history data, can be used as features as well.

At step 328, patient-specific hemodynamic indices are computed based on the extracted features using the trained surrogate model. The trained surrogate model is a data driven model trained from the synthetic training data using the blood flow simulation results computed using the multi-scale model of renal arterial circulation. The trained surrogate model inputs the extracted features, including the geometric features, non-invasive measurement features, and demographic data features, and calculates hemodynamic indices (such as rFFR or trans-stenotic pressure gradient) for particular locations in the patient-specific renal arterial geometry based on the extracted features. In order to compute a hemodynamic index for a particular location in the patient-specific renal arterial geometry, the trained surrogate model can be trained to consider geometric features (e.g., renal insufficiency scores, renal insufficiency weights, geometric measurements) extracted upstream and downstream of the current location, in addition to features extracted at that location. In one embodiment, the trained surrogate model can automatically compute the hemodynamic indices for a plurality of locations without any user input. For example, the trained surrogate model can automatically compute hemodynamic indices for all centerline points of the patient-specific renal artery centerline, a plurality of locations automatically sampled from the centerline points of the patient-specific renal artery centerline (e.g., skip every n centerline points), or at locations corresponding to each of the renal artery stenosis regions in the patient-specific renal arterial geometry. In another embodiment, the user may input a location, for example by clicking on the location on a display device of computer system, and the trained surrogate model can compute the patient-specific hemodynamic index (e.g., rFFR, trans-stenotic pressure gradient, etc.) at the input location in real time in response to receiving the user input. Multiple trained surrogate models may be used to compute multiple hemodynamic indices at locations in the patient-specific renal arterial geometry. For example, separate trained surrogate models may be used for computing rFFR at rest, rFFR at hyperemia, average trans-stenotic pressure gradient at rest, average trans-stenotic pressure gradient at hyperemia, peak trans-stenotic pressure gradient at rest, peak trans-stenotic pressure gradient at hyperemia, and other hemodynamic indices.

At step 330, the patient-specific hemodynamic indices computed by the trained surrogate model are output. For example, values for such indices may be displayed on a display device. When a hemodynamic index is computed by the trained surrogate model in response to a user input identifying a location, the value for the hemodynamic index can be displayed in real time to the user. In a possible implementation, the values for a hemodynamic index for one or more locations can be displayed by overlaying those values at their corresponding locations on a displayed image of the patient-specific renal arterial centerline or on the displayed medical image data of the patient. When hemodynamic indices for multiple locations are automatically computed using the trained surrogate model an image showing the locations and the corresponding values for the hemodynamic indices may be automatically displayed. In a possible implementation a color-coded visualization of the patient-specific renal arterial centerline may be displayed in which locations on the renal arterial centerline are color coded based on a severity of the hemodynamic index (e.g., rFFR).

Figure 4:
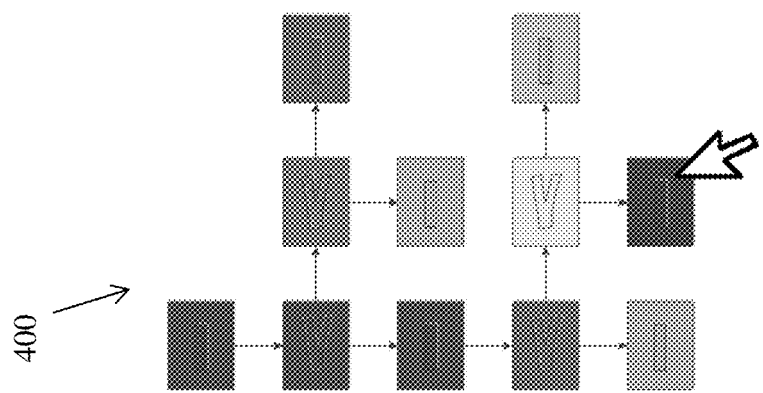
FIG. 4 illustrates an exemplary schematic graph for visualizing a renal arterial tree and computed hemodynamic index.

The computed renal hemodynamic indices can be visualized on the scanner (image acquisition device), or on another device, such as an imaging workstation. In an exemplary implementation, any point on the image can be queried (point & click) for the associated value of any feature, and the corresponding value is shown overlaid on the image. In an exemplary implementation, a user can activate a "no click" mode, in which case the hemodynamic index is displayed in correspondence to the cursor position by just positioning the cursor on the position of interest. The display device may provide a touch screen, enabling interactions with the anatomical object of interest (gestures to rotate, zoom, pan). Point & touch inputs can cause the device to display the hemodynamic value of interest at the point of touch. In a possible implementation, an eye-tracking device may be provided, so that the hemodynamic value of interest is displayed at the location that is being observed by the user. In an exemplary embodiment, the renal arterial tree can be represented as an abstract graph (or tree), which can be color coded based on the hemodynamic index of interest. The traversal of the schematic graph can be automatically synced with the traversal of the image (point-to-point correspondence). FIG. 4 illustrates an exemplary schematic graph for visualizing a renal arterial tree and computed hemodynamic index. As shown in FIG. 4, the graph 400 displays the renal arterial geometry as separate segments, each of which is color coded based on the computed hemodynamic index for that segment. As a user traverses the graph, the graph is automatically synced with the medical image data and the corresponding point in the medical image data is displayed.

Figure 5:
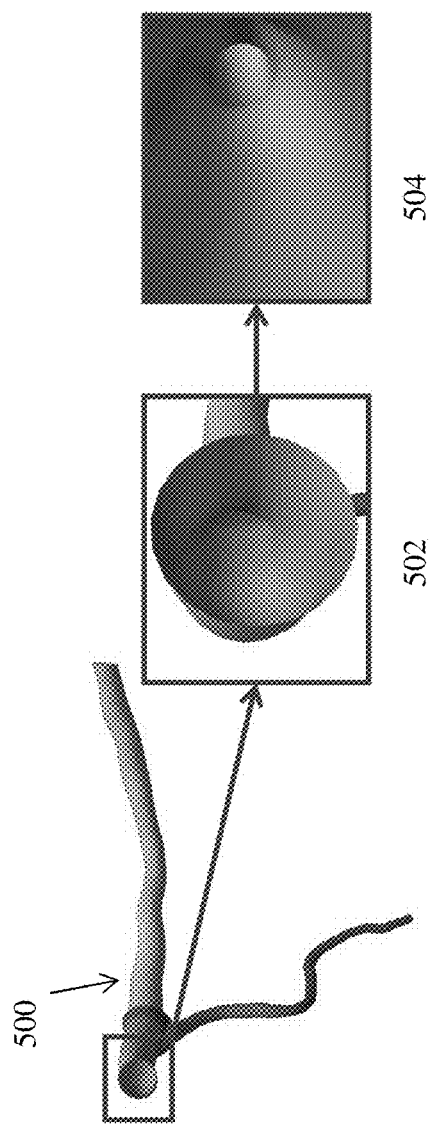
FIG. 5 illustrates an exemplary "fly-through" visualization of the renal arterial tree.

FIG. 5 illustrates an exemplary "fly-through" visualization of the renal arterial tree. Based on the extracted patient-specific geometry of the renal arterial tree, the renal arterial tree can be represented as a three dimensional structure that can be visualized and interactively navigated through. The surface of the synthetic three dimensional structure can be color coded based on the computed hemodynamic index. As shown in FIG. 5, a 3D representation 500 of the renal artery is displayed. Images 502 and 504 show navigation by "flying through" the 3D representation 500.

Figure 6:
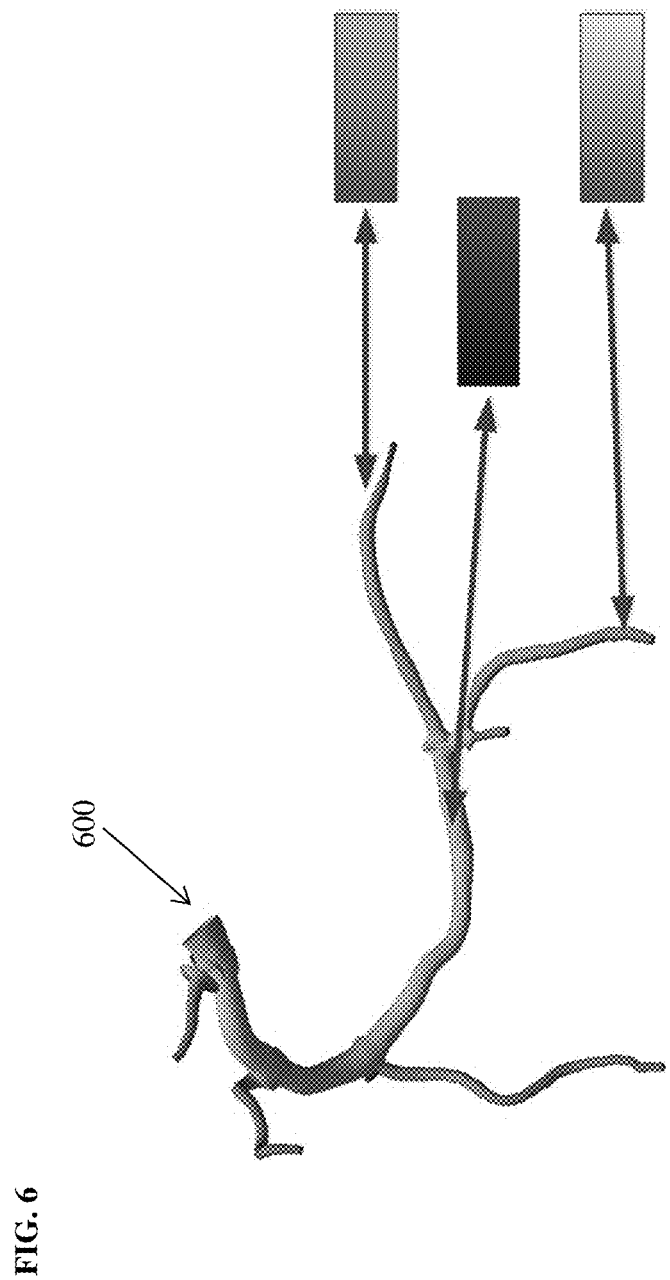
FIG. 6 illustrates an example of an unfolded view of a renal arterial tree.

FIG. 6 illustrates an example of an unfolded view of a renal arterial tree. As shown in FIG. 6, each vessel can be mapped to a plane and represented in an "unfolded" view 600. In this view, the renal arterial tree looks like a 2D tree. Each vessel can be color coded by the computed hemodynamic index of interest. In this representation, additional information on the vessel can also be visualized (e.g., endothelial function, wall shear stress, plaque burden).

In another possible embodiment, the renal arterial tree can be mapped to an atlas or a pictorial representation of the anatomical structure, which can be color coded based on the value of the feature of interest. The navigation of the atlas can be automatically synchronized with navigation of the medical image.

Figure 7:
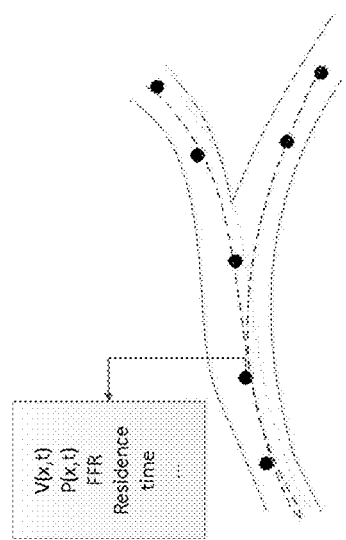
FIG. 7 illustrates an exemplary visualization in which particles are displayed inside of a vessel of interest and the hemodynamic index of interest is visualized for each particle.

FIG. 7 illustrates an exemplary visualization in which particles are displayed inside of a vessel of interest and the hemodynamic index of interest is visualized for each particle. As shown in FIG. 7, one or more particles (glyphs) are displayed moving (or fixed) along the centerline. It is also possible that such particles (glyphs) can be displayed directly in the medical image of the patient. Each point can be assigned a color associated with the value of the hemodynamic index of interest at that point. The same particles (glyphs) can be associated with the statistics of the features of interest, evaluated at the location of the particle.

Figure 8:
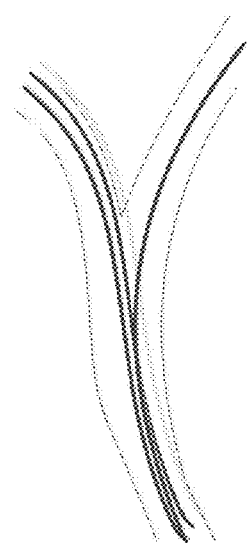
FIG. 8 illustrates an exemplary visualization in which centerlines of the vessels of interest are visualized and color coded based on values of the hemodynamic indices of interest.
Figure 9:
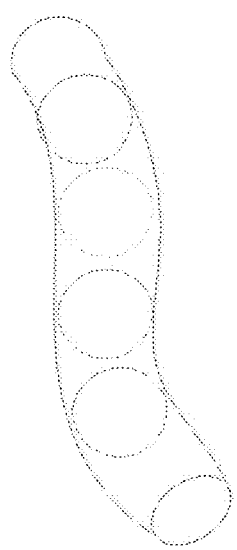
FIG. 9 illustrates an exemplary visualization in which cross-sections of the vessel of interest are displayed and color coded based on the value of the hemodynamic index of interest.

FIG. 8 illustrates an exemplary visualization in which centerlines of the vessels of interest are visualized and color coded based on values of the hemodynamic indices of interest. FIG. 9 illustrates an exemplary visualization in which cross-sections of the vessel of interest are displayed and color coded based on the value of the hemodynamic index of interest. In another possible implementation, flow pathlines or streamlines, which are color coded based on the hemodynamic index of interest, can be displayed. The image of the renal arterial tree can be color coded based on any feature extracted during the pre-processing (feature extraction) phase or based on any computed hemodynamic index. In an advantageous embodiment, the computed rFFR value can be used to color the renal arterial tree.

According to an advantageous embodiment, since synthetic training data is used to train the data-driven surrogate model, the training database can be vastly expanded at little additional cost. Although a very large number of synthetic cases can be generated for training the machine-learning based surrogate model, these cases may not cover all patient-specific cases. Hence, when applying the trained surrogate model to predict results for patient-specific data in the prediction phase, some features computed for the patient-specific data may have values which are outside of the range of values covered by the synthetic database. For example, in the prediction phase (320 of FIG. 3), a patient-specific renal arterial geometry with one or more geometric features outside a range of the features extracted from the synthetic training database may be identified. In particular, when the geometric features (e.g., renal insufficiency weights, renal insufficiency scores, geometric measurements of stenoses) are extracted for a patient-specific renal arterial geometry, the geometric features can be compared to a range of features extracted from all of the synthetic renal arterial anatomical models in the synthetic training database to determine if any of the features from the patient-specific renal arterial geometry fall outside the range of the corresponding features in the synthetic training database. In this case, new synthetic renal arterial anatomical models can be generated having feature values similar to the features of the identified patient-specific renal arterial geometry. For example, multiple new synthetic renal arterial trees may be generated to span feature values between the previous range of features in the synthetic training database and the new feature outside of the previous range. The data-driven surrogate model can then be re-trained on the entire expanded synthetic training database using a machine learning algorithm. This results in an updated ad improved trained surrogate model that can then be used to perform the prediction phase to predict the hemodynamic indices.

The real-time performance of the method of FIG. 3, as well as the fact that it relies on a synthetically generated training database, which can be expanded on-demand and virtually without limit, makes this method advantageous for therapy planning applications. One of the therapies widely used for treating arterial stenosis is stenting, i.e. the placement of a metal or polymer stent in the artery to open up the lumen, and hence facilitate the flow of blood. When dealing with renal artery stenosis, the stenting therapy is referred to as PRI—Percutaneous Renal Intervention. This is an example of an intervention that aims at restoring the healthy function of the arterial tree by altering its geometry, and as such can be naturally described based on the geometric features used by our method. For example, any system for the virtual placement of the stent in an anatomical geometrical model extracted from medical images can be coupled with the machine-learning based surrogate model. The trained surrogate model can compute all hemodynamic quantities of interest that would result from each candidate therapy option, therefore predicting the outcome of PCI, and allowing the planning of an optimal PRI procedure.

According to an advantageous embodiment, instead of performing a virtual placement of the stent in the anatomical model extracted from medical images, the features used by the machine learning algorithm may be directly adapted to account for the effect of the treatment. Thus, first the features are determined for the original patient-specific anatomical model, next they are adapted, either automatically or by using information input by the user (for example, the user may specify different levels for the success of the treatment: partially successful treatment of the stenosis region, fully successful treatment of the stenosis region, etc.), and finally the machine learning based trained surrogate model is applied to compute the post-treatment hemodynamic index. For example, the features may be directly adapted to account for the effect of the treatment by adjusting the renal insufficiency scores. In a possible implementation, the renal insufficiency scores may be adapted by using different formulations for the mathematical operators $f_4$ and $f_5$, which would lead to smaller renal insufficiency scores. In terms of the machine learning algorithm based trained surrogate model, either the same trained surrogate model used for the pre-treatment predictions may be used, or a different machine learning trained surrogate model may be trained on synthetic cases representative of post-treatment geometries and used for predicting post-treatment hemodynamic indices.

In a possible extension to the method of FIG. 3, the hemodynamic index (e.g., rFFR) estimated at a location upstream from a current location using the trained surrogate model can also be used as a feature for computing the hemodynamic index at the current location by the trained surrogate model.

According to an advantageous embodiment of the present invention, the sensitivity of the hemodynamic index with respect to one or more of the features may be determined by using the trained machine learning based surrogate model by varying the features in a certain range. It is also possible that the sensitivity of the hemodynamic index with respect to one or more of the features may be predicted using a different trained surrogate model trained using a different machine learning algorithm. The sensitivity of the hemodynamic index with respect to one or more of the features can be computed and visualized for the patient-specific data during the prediction phase by varying the one or more geometric features within a predetermined range and computing the hemodynamic index with the trained surrogate model. This information can be used to inform the user and/or the machine learning algorithm of which geometric features are more relevant to the accuracy of the prediction of the hemodynamic index.

As described above, the method of FIG. 3 uses the patient specific multiscale model of renal arterial circulation to simulate the renal arterial blood flow. However, in an alternative embodiment, this multiscale model can be replaced with a physics-based model of renal blood flow including the RAAS system (e.g., a purely lumped parameter model). The methodologies described herein may be used together with any imaging modality. If MRI is used, PC-MRI based flow rates and velocities may be used to extract additional features for the prediction of patient-specific measures. The proposed framework may also be similarly applied for predicting patient-specific hemodynamic functional diagnostic indices at other locations inside the cardiovascular system, such as the heart, iliac arteries, carotid arteries, abdominal aorta, descending aorta, etc.

The above-described methods for personalized non-invasive assessment of renal artery stenosis from medical image data of can be implemented on a computer using well-known computer processors, memory units, storage devices, computer software, and other components. A high-level block diagram of such a computer is illustrated in FIG. 10. Computer 1002 contains a processor 1004, which controls the overall operation of the computer 1002 by executing computer program instructions which define such operation. The computer program instructions may be stored in a storage device 1012 (e.g., magnetic disk) and loaded into memory 1010 when execution of the computer program instructions is desired. Thus, the steps of the methods of FIG. 3 may be defined by the computer program instructions stored in the memory 1010 and/or storage 1012 and controlled by the processor 1004 executing the computer program instructions. An image acquisition device 1020, such as a CT scanning device, MR scanning device, Ultrasound device, etc., can be connected to the computer 1002 to input image data to the computer 1002. It is possible to implement the image acquisition device 1020 and the computer 1002 as one device. It is also possible that the image acquisition device 1020 and the computer 1002 communicate wirelessly through a network. In a possible implementation, the computer 1002 may be located remotely from the image acquisition device and may perform one or more of the method steps as a cloud-based or server-based service. The computer 1002 also includes one or more network interfaces 1006 for communicating with other devices via a network. The computer 1002 also includes other input/output devices 1008 that enable user interaction with the computer 1002 (e.g., display, keyboard, mouse, speakers, buttons, etc.). One skilled in the art will recognize that an implementation of an actual computer could contain other components as well, and that FIG. 10 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method, comprising:
receiving medical image data of the patient;
extracting patient-specific renal arterial geometry of the patient from the medical image data;
extracting features from the patient-specific renal arterial geometry of the patient, the extracted features from the patient-specific renal arterial geometry comprising renal insufficiency weights and renal insufficiency scores for renal artery segments, wherein a renal insufficiency weight for a particular renal artery segment is based on renal insufficiency weights for downstream renal artery segments; and
computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries.

2. The method of claim 1, further comprising receiving at least one of non-invasive physiological measurements of the patient or demographic data of the patient, wherein computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
computing the hemodynamic index for the one or more locations of interest in the patient-specific renal arterial geometry based on the extracted features from the patient-specific renal arterial geometry and based on features corresponding to the at least one of the non-invasive physiological measurements of the patient or the demographic data of the patient using the trained machine-learning based surrogate model.

3. The method of claim 1, further comprising receiving one or more renal biomarkers of the patient, wherein computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
computing the hemodynamic index for the one or more locations of interest in the patient-specific renal arterial geometry based on the extracted features from the patient-specific renal arterial geometry and based on features corresponding to the one or more renal biomarkers of the patient using the trained machine-learning based surrogate model.

4. The method of claim 1, wherein the trained machine-learning based surrogate model is trained based on the features extracted from the synthetically generated renal arterial tree geometries and renal blood flow simulation results obtained from renal blood flow simulations performed using a respective patient-specific multi-scale model of renal circulation including a model of a renin-angiotensin-aldosterone system (RAAS) for each of the synthetically generated renal arterial geometries.

5. The method of claim 1, wherein extracting features from the patient-specific renal arterial geometry of the patient comprises:
calculating the renal insufficiency weights for first renal artery segments based on the patient-specific renal arterial geometry; and
calculating the renal insufficiency scores for second renal artery segments based on the renal insufficiency weights.

6. The method of claim 5, wherein calculating the renal insufficiency weights for first renal artery segments based on the patient-specific renal arterial geometry comprises:
individually calculating initial local renal insufficiency weights for each of the first renal artery segments based on a respective reference radius value calculated for each of the first renal artery segments;
calculating a global renal insufficiency weight for an entire renal arterial tree based on the initial local renal insufficiency weights for the first renal artery segments; and
calculating final local renal insufficiency weights for each of the first renal artery segments by distributing the global renal insufficiency weight over the first renal artery segments.

7. The method of claim 6, wherein calculating a global renal insufficiency weight for an entire arterial tree based on the initial local renal insufficiency weights for the first renal artery segments comprises:
calculating a plurality of global renal insufficiency weight estimates for the entire renal arterial tree, wherein each of the plurality of global renal insufficiency weight estimates is calculated from initial local renal insufficiency weights of the first renal artery segments from a respective one of a plurality of generations of the first renal artery segments; and
calculating the global renal insufficiency weight of the entire renal arterial tree based on the plurality of global renal insufficiency weight estimates.

8. The method of claim 6, wherein calculating final local renal insufficiency weights for each of the first renal artery segments by distributing the global renal insufficiency weight over the first renal artery segments comprises:
calculating the final local renal insufficiency weights of a plurality of leaf renal artery segments by distributing the global renal insufficiency weight over the leaf renal artery segments based on the initial local renal insufficiency weights of the leaf renal artery segments; and
calculating the final local renal insufficiency weight for each remaining one of the first renal artery segments as a sum of the final local renal insufficiency weights of leaf segments downstream from that renal artery segment.

9. The method of claim 5, wherein calculating the renal insufficiency scores for second renal artery segments based on the renal insufficiency weights comprises:
dividing the second renal artery segments into non-anomalous portions and anomalous portions;
calculating the renal insufficiency scores for each non-anomalous portion based on a spatially varying radius of the non-anomalous portion and the renal insufficiency weight of the renal artery segment in which the non-anomalous portion is located; and
calculating the renal insufficiency scores for each anomalous portion based on a first product of the renal insufficiency weight of the renal artery segment in which the anomalous portion is located and a first mathematical operator applied to a spatially varying radius of the anomalous portion and a second product of a squared renal insufficiency weight of the renal artery segment in which the anomalous portion is located and a second mathematical operator applied to the spatially varying radius of the anomalous portion.

10. The method of claim 9, wherein extracting features from the patient-specific renal arterial geometry of the patient further comprises:
for each of the one or more locations of interest, calculating one or more of a cumulative renal insufficiency score from all renal segments lying between a root segment and the current location, a cumulative renal insufficiency score from the non-anomalous portions of renal artery segments lying between the root segment and the current location, a cumulative renal insufficiency score from the anomalous portions of renal artery segments lying between the root segment and the current location, a cumulative renal insufficiency score from all renal artery segments lying between the current location and a leaf segment, a cumulative renal insufficiency score from the non-anomalous portions of renal artery segments lying between the current location and a leaf segment, or a cumulative renal insufficiency score from the anomalous portions of renal artery segments lying between the current location and a leaf segment.

11. The method of claim 1, wherein extracting features from the patient-specific renal arterial geometry of the patient further comprises:
extracting a plurality of geometric measurements for one or more renal artery stenosis regions in the patient-specific renal arterial geometry of the patient.

12. The method of claim 1, wherein the one or more locations of interest correspond to one or more renal artery stenosis locations, computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
automatically computing the hemodynamic index for the one or more renal artery stenosis locations in the patient-specific renal arterial geometry based on the extracted features from the patient-specific renal arterial geometry using the trained machine-learning based surrogate model.

13. The method of claim 1, wherein computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
computing the hemodynamic index for the one or more locations of interest in the patient-specific renal arterial geometry in response to a user input identifying the one or more locations of interest.

14. The method of claim 1, wherein the hemodynamic index is renal fractional flow reserve (rFFR) at rest or at hyperemia.

15. The method of claim 1, wherein the hemodynamic index is a trans-stenotic pressure gradient at rest or at hyperemia.

16. The method of claim 1, wherein computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
computing a plurality of hemodynamic indices for each of the one or more locations of interest in the patient-specific renal arterial geometry based on the extracted features from the patient-specific renal arterial geometry using a respective one of a plurality of trained machine-learning based surrogate models trained based on the features extracted from the synthetically generated renal arterial tree geometries.

17. The method of claim 1, further comprising:
displaying a visualization of the patient-specific renal arterial geometry color coded based on the hemodynamic index computed for the one or more locations of interest in the patient-specific renal arterial geometry.

18. An apparatus, comprising:
means for receiving medical image data of the patient;
means for extracting patient-specific renal arterial geometry of the patient from the medical image data;
means for extracting features from the patient-specific renal arterial geometry of the patient, the extracted features from the patient-specific renal arterial geometry comprising renal insufficiency weights and renal insufficiency scores for renal artery segments, wherein a renal insufficiency weight for a particular renal artery segment is based on renal insufficiency weights for downstream renal artery segments; and
means for computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries.

19. The apparatus of claim 18, wherein the means for computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
means for computing the hemodynamic index for the one or more locations of interest in the patient-specific renal arterial geometry based on the extracted features from the patient-specific renal arterial geometry and based on features corresponding to at least one of non-invasive physiological measurements of the patient or demographic data of the patient using the trained machine-learning based surrogate model.

20. The apparatus of claim 18, wherein the means for computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
means for computing the hemodynamic index for the one or more locations of interest in the patient-specific renal arterial geometry based on the extracted features from the patient-specific renal arterial geometry and based on features corresponding to one or more renal biomarkers of the patient using the trained machine-learning based surrogate model.

21. The apparatus of claim 18, wherein the trained machine-learning based surrogate model is trained based on the features extracted from the synthetically generated renal arterial tree geometries and renal blood flow simulation results obtained from renal blood flow simulations performed using a respective patient-specific multi-scale model of renal circulation including a model of a renin-angiotensin-aldosterone system (RAAS) for each of the synthetically generated renal arterial geometries.

22. The apparatus of claim 18, wherein the means for extracting features from the patient-specific renal arterial geometry of the patient comprises:
means for calculating the renal insufficiency weights for first renal artery segments based on the patient-specific renal arterial geometry; and
means for calculating the renal insufficiency scores for second renal artery segments based on the renal insufficiency weights.

23. The apparatus of claim 18, wherein the means for extracting features from the patient-specific renal arterial geometry of the patient further comprises:
means for extracting a plurality of geometric measurements for one or more renal artery stenosis regions in the patient-specific renal arterial geometry of the patient.

24. The apparatus of claim 18, wherein the hemodynamic index is renal fractional flow reserve (rFFR) at rest or at hyperemia.

25. The apparatus of claim 18, wherein the hemodynamic index is a trans-stenotic pressure gradient at rest or at hyperemia.

26. The apparatus of claim 18, wherein the means for computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
means for computing a plurality of hemodynamic indices for each of the one or more locations of interest in the patient-specific renal arterial geometry based on the extracted features from the patient-specific renal arterial geometry using a respective one of a plurality of trained machine-learning based surrogate models trained based on the features extracted from the synthetically generated renal arterial tree geometries.

27. The apparatus of claim 18, further comprising:
means for displaying a visualization of the patient-specific renal arterial geometry color coded based on the hemodynamic index computed for the one or more locations of interest in the patient-specific renal arterial geometry.

28. A non-transitory computer readable medium storing computer program instructions, the computer program instructions when executed by a processor cause the processor to perform operations comprising:
receiving medical image data of the patient;
extracting patient-specific renal arterial geometry of the patient from the medical image data;
extracting features from the patient-specific renal arterial geometry of the patient, the extracted features from the patient-specific renal arterial geometry comprising renal insufficiency weights and renal insufficiency scores for renal artery segments, wherein a renal insufficiency weight for a particular renal artery segment is based on renal insufficiency weights for downstream renal artery segments; and
computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries.

29. The non-transitory computer readable medium of claim 28, wherein computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
computing the hemodynamic index for the one or more locations of interest in the patient-specific renal arterial geometry based on the extracted features from the patient-specific renal arterial geometry and based on features corresponding to at least one of non-invasive physiological measurements of the patient or demographic data of the patient using the trained machine-learning based surrogate model.

30. The non-transitory computer readable medium of claim 28, wherein computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
computing the hemodynamic index for the one or more locations of interest in the patient-specific renal arterial geometry based on the extracted features from the patient-specific renal arterial geometry and based on features corresponding to one or more renal biomarkers of the patient using the trained machine-learning based surrogate model.

31. The non-transitory computer readable medium of claim 28, wherein the trained machine-learning based surrogate model is trained based on the features extracted from the synthetically generated renal arterial tree geometries and renal blood flow simulation results obtained from renal blood flow simulations performed using a respective patient-specific multi-scale model of renal circulation including a model of a renin-angiotensin-aldosterone system (RAAS) for each of the synthetically generated renal arterial geometries.

32. The non-transitory computer readable medium of claim 28, wherein extracting features from the patient-specific renal arterial geometry of the patient comprises:
calculating the renal insufficiency weights for first renal artery segments based on the patient-specific renal arterial geometry; and
calculating the renal insufficiency scores for second renal artery segments based on the renal insufficiency weights.

33. The non-transitory computer readable medium of claim 28, wherein extracting features from the patient-specific renal arterial geometry of the patient further comprises:
extracting a plurality of geometric measurements for one or more renal artery stenosis regions in the patient-specific renal arterial geometry of the patient.

34. The non-transitory computer readable medium of claim 28, wherein the one or more locations of interest correspond to one or more renal artery stenosis locations, computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
automatically computing the hemodynamic index for the one or more renal artery stenosis locations in the patient-specific renal arterial geometry based on the extracted features from the patient-specific renal arterial geometry using the trained machine-learning based surrogate model.

35. The non-transitory computer readable medium of claim 28, wherein computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
computing the hemodynamic index for the one or more locations of interest in the patient-specific renal arterial geometry in response to a user input identifying the one or more locations of interest.

36. The non-transitory computer readable medium of claim 28, wherein the hemodynamic index is renal fractional flow reserve (rFFR) at rest or at hyperemia.

37. The non-transitory computer readable medium of claim 28, wherein the hemodynamic index is a trans-stenotic pressure gradient at rest or at hyperemia.

38. The non-transitory computer readable medium of claim 28, wherein computing a hemodynamic index for one or more locations of interest in the patient-specific renal arterial geometry based on the extracted features from the patient-specific renal arterial geometry using a trained machine-learning based surrogate model trained based on features extracted from synthetically generated renal arterial tree geometries comprises:
computing a plurality of hemodynamic indices for each of the one or more locations of interest in the patient-specific renal arterial geometry based on the extracted features from the patient-specific renal arterial geometry using a respective one of a plurality of trained machine-learning based surrogate models trained based on the features extracted from the synthetically generated renal arterial tree geometries.

39. The non-transitory computer readable medium of claim 28, wherein the operations further comprise:
displaying a visualization of the patient-specific renal arterial geometry color coded based on the hemodynamic index computed for the one or more locations of interest in the patient-specific renal arterial geometry.

* * * * *